US010626093B2

(12) United States Patent
Suri et al.

(10) Patent No.: US 10,626,093 B2
(45) Date of Patent: Apr. 21, 2020

(54) POLYMORPHIC FORM OF CRYSTALLINE ROSUVASTATIN CALCIUM AND NOVEL PROCESSES FOR CRYSTALLINE AS WELL AS AMORPHOUS ROSUVASTATIN CALCIUM

(71) Applicant: MOREPEN LABORATORIES LIMITED, Himachal Pradesh (IN)

(72) Inventors: Sanjay Suri, Himachal Pradesh (IN); Pal Madan Tanwar, Himachal Pradesh (IN); Kumar Suman Sharma, Himachal Pradesh (IN); Kumar Sanjay Mishra, Himachal Pradesh (IN); Avinash Aggarwal, Himachal Pradesh (IN)

(73) Assignee: MOREPEN LOBORATORIES LIMITED, Himachal Pradesh (IN)

( * ) Notice: Subject to any disclaimer, the term of this patent is extended or adjusted under 35 U.S.C. 154(b) by 0 days.

(21) Appl. No.: 16/094,243

(22) PCT Filed: Jun. 7, 2016

(86) PCT No.: PCT/IN2016/000145
§ 371 (c)(1),
(2) Date: Oct. 17, 2018

(87) PCT Pub. No.: WO2017/183040
PCT Pub. Date: Oct. 26, 2017

(65) Prior Publication Data
US 2019/0127334 A1 May 2, 2019

(30) Foreign Application Priority Data
Apr. 18, 2016 (IN) .............................. 201613013389

(51) Int. Cl.
*C07D 239/42* (2006.01)
(52) U.S. Cl.
CPC ........ *C07D 239/42* (2013.01); *C07B 2200/13* (2013.01)
(58) Field of Classification Search
CPC .................................................... C07D 239/42
See application file for complete search history.

(56) References Cited

U.S. PATENT DOCUMENTS 6,777,552 B2 8/2004 Niddam-Hildesheim et al.
2008/0194604 A1 8/2008 Blatter et al.

FOREIGN PATENT DOCUMENTS

| EP | 0521471 A1 | 1/1993 | |
|---|---|---|---|
| WO | 2000042024 A1 | 7/2000 | |
| WO | 2005023779 A1 | 3/2005 | |
| WO | 2012011129 A2 | 1/2012 | |
| WO | WO2012011129 | * 1/2012 | ........... C07D 239/42 |

OTHER PUBLICATIONS

International Search Report, PCT/IN2016000145, dated Aug. 31, 2016.

* cited by examiner

*Primary Examiner* — Paul V Ward
(74) *Attorney, Agent, or Firm* — Porzio Bromberg & Newman

(57) ABSTRACT

The present invention relates to new polymorphic forms of Crystalline Rosuvastatin calcium along with novel processes for crystalline as well as amorphous Rosuvastatin calcium.

14 Claims, 4 Drawing Sheets

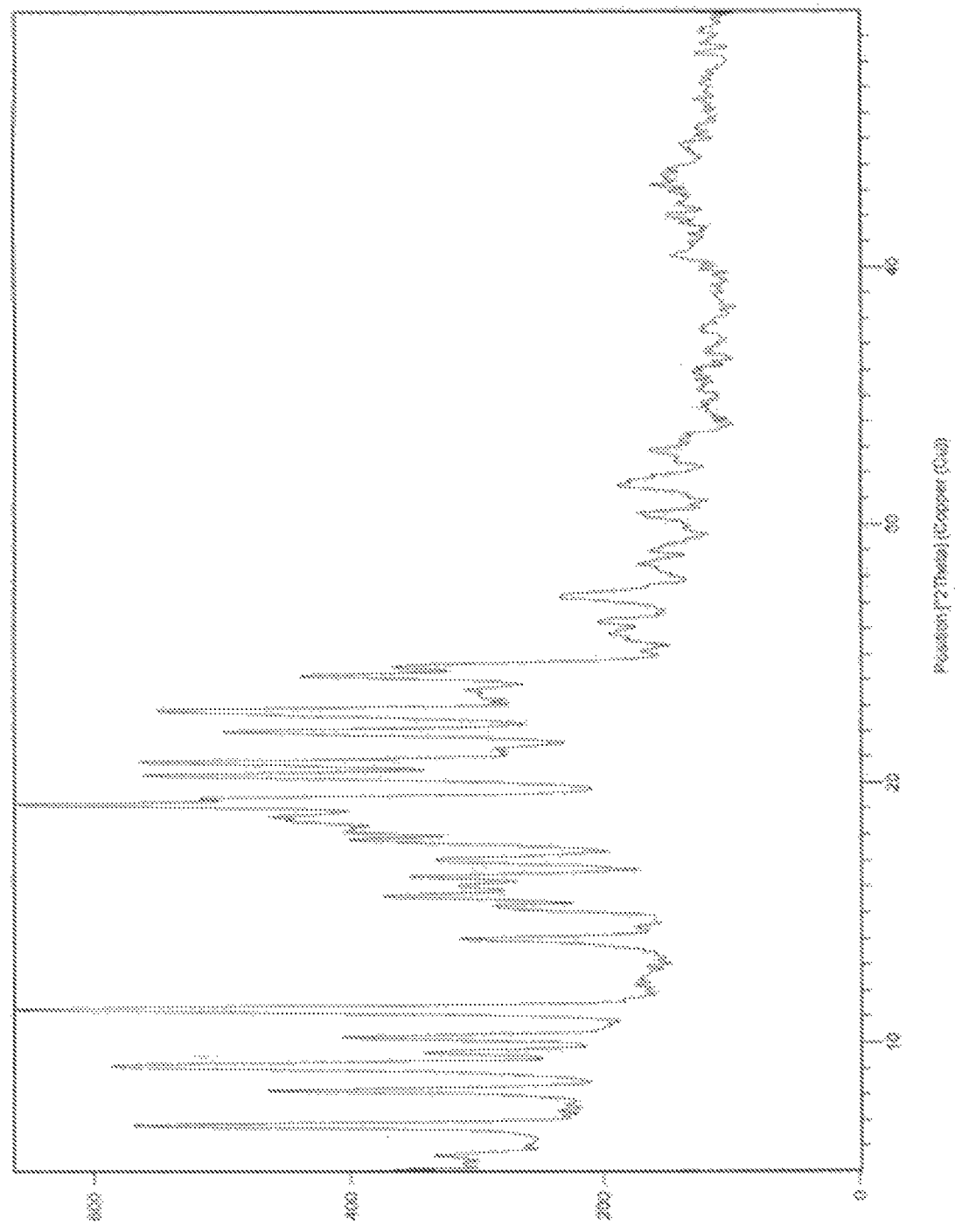
FIGURE 1 (Form M, Ratio 10:5 of Acetone:water)

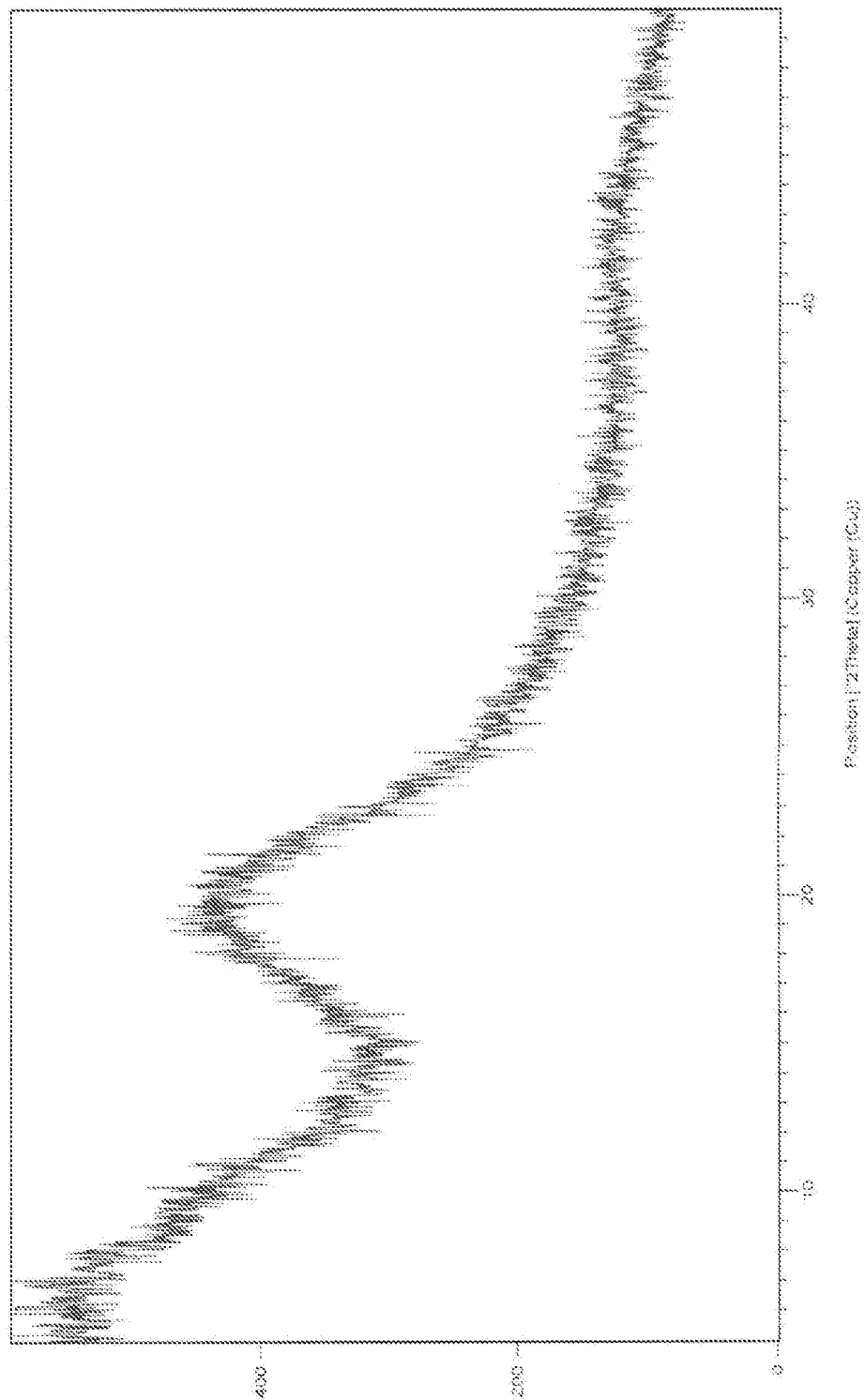
FIGURE 2 (Amorphous)

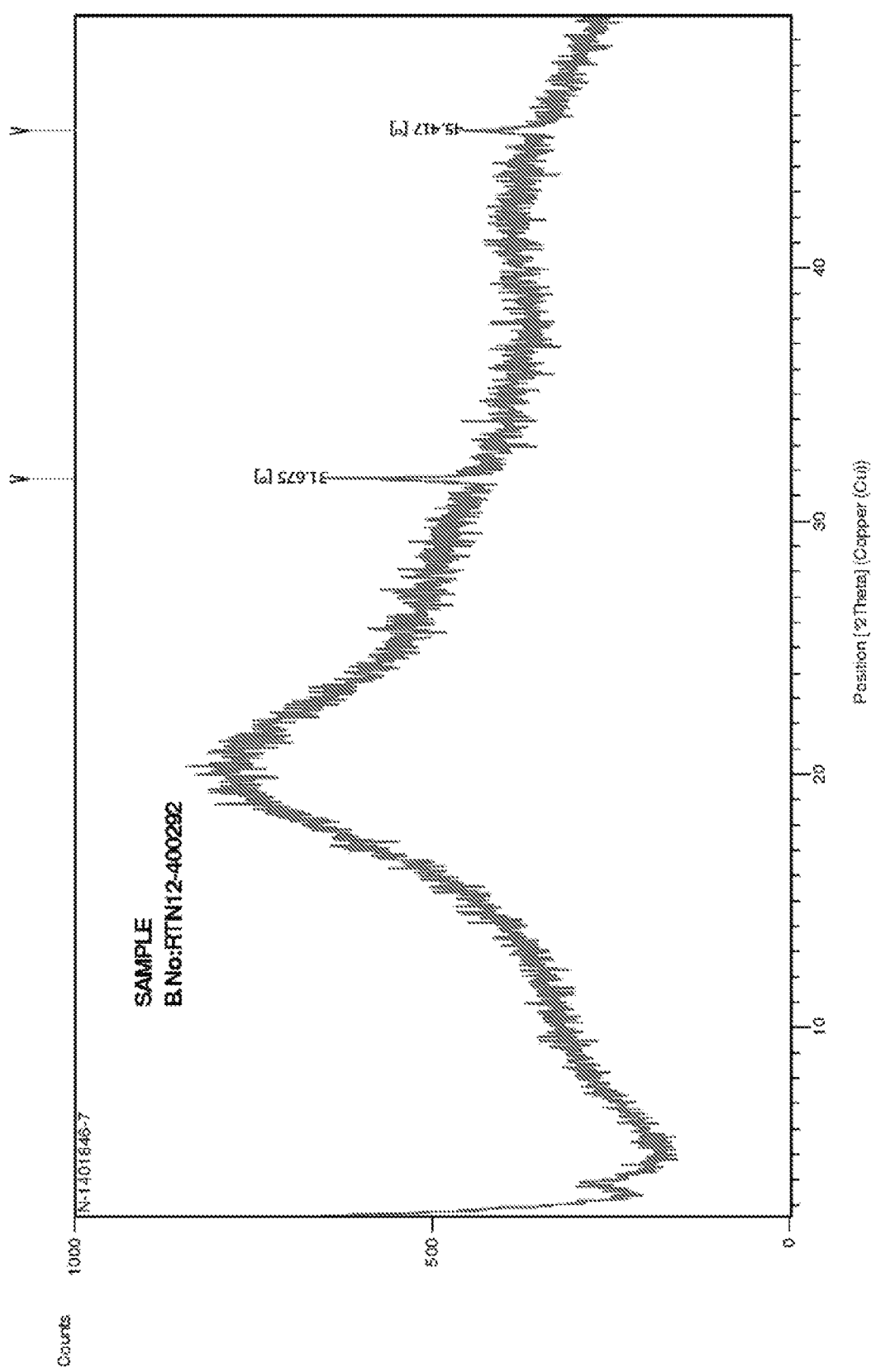
FIGURE 3 (Form M2)

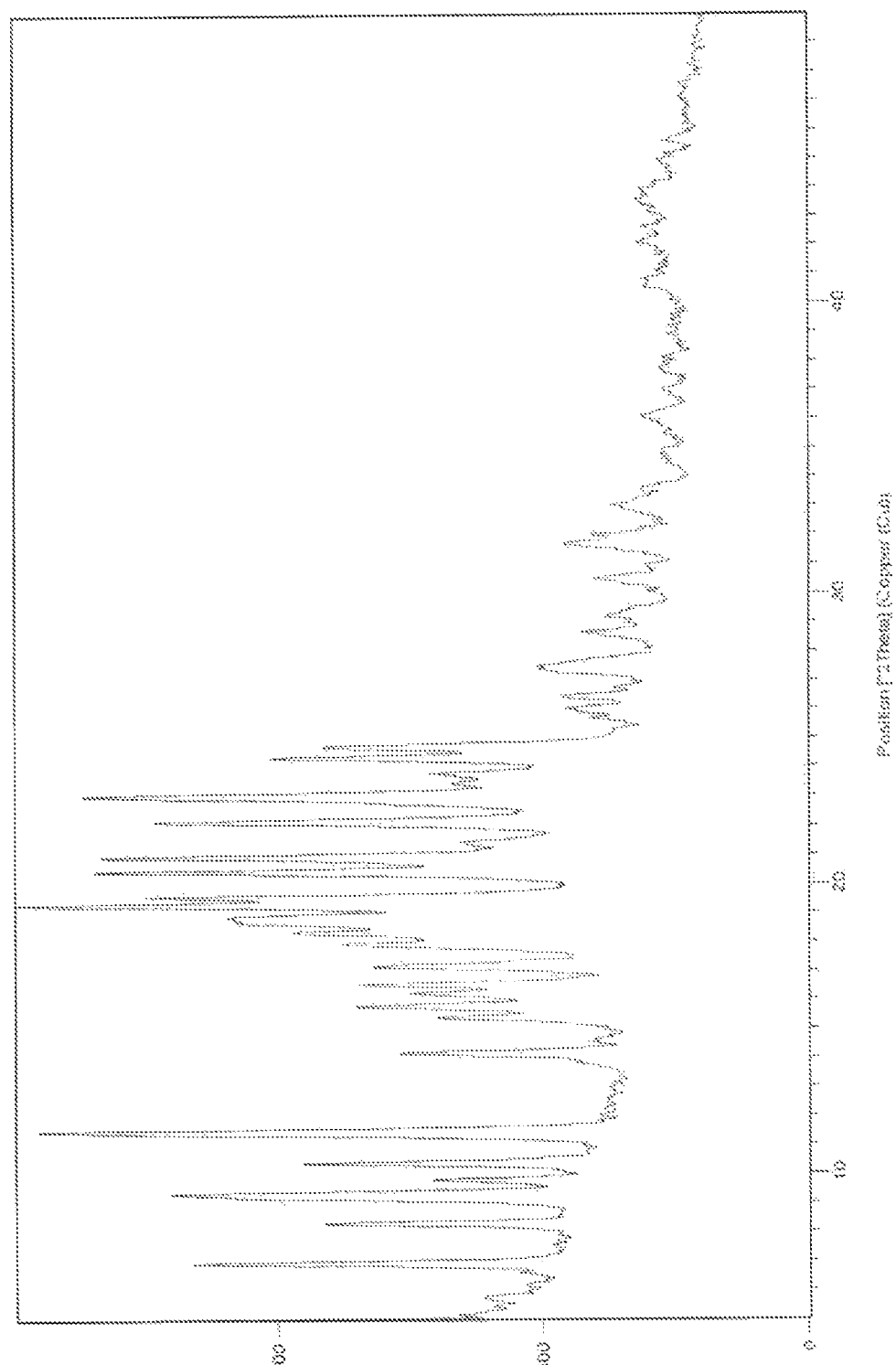
FIGURE 4 (FORM M, Ratio 5:5 of Acetone:water)

POLYMORPHIC FORM OF CRYSTALLINE ROSUVASTATIN CALCIUM AND NOVEL PROCESSES FOR CRYSTALLINE AS WELL AS AMORPHOUS ROSUVASTATIN CALCIUM

REFERENCE

This application is a Patent of Addition filed under section 54 and rule 13(3) of the Indian Patents Act, 1970 to Indian Patent Application No.: 1556/DEL/2011 filed on Jun. 1, 2011, the contents of which are being incorporated herein by reference. The invention comprises an improvement in and a modification of the invention claimed in the specification of the main patent applied for.

FIELD OF INVENTION

The present invention relates to new polymorphic of crystalline Rosuvastatin calcium, furthermore the present invention also reports novel processes for crystalline as well as amorphous form of Rosuvastatin calcium which are used to treat a disease condition wherein inhibition of HMG COA reductase is beneficial.

BACKGROUND OF INVENTION

Rosuvastatin calcium is known by its chemical name as 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt of formula I as given below.

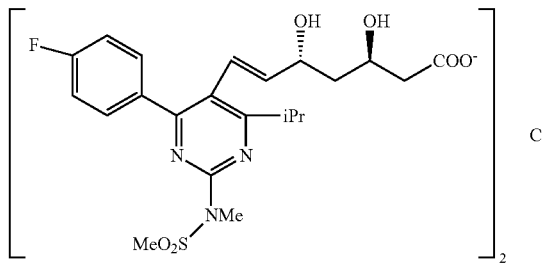

FORMULA I which is known to inhibit the HMG-CoA reductase, and subsequently suppress the bio synthesis of cholesterol. Rosuvastatin calcium is useful in the treatment of hyper cholesterolemia, hyperlipoproteinemia, and atherosclerosis. Rosuvastatin calcium may form hydrates with a varying content of water.

EP-A1-0521471 describes in the preparation of Rosuvastatin calcium in powder form. Rosuvastatin sodium is dissolved in water at room temperature and an aqueous calcium chloride solution is added dropwise. The collected precipitate is an amorphous powder. U.S. Pat. No. 6,777,552 discloses the preparation of Rosuvastatin calcium through hydrolysis of methyl 7-[4-(4-fluorophenyl)-6-isopropyl-2-[methyl(methylsulfonyl)amino] pyrimidin-5-yl]-(3R,5S)-3,5-dihydroxy-(E)-6-heptanoate with calcium hydroxide in a water/ethanol solution.

WO 00/42024 discloses a crystalline form, hereafter referred to as Form A of -[4-(4-flurophenyl)-6-isopropyl-2-(N-methyl-N-methyl sulfonyl amino)-pyrimidin-5-yl]-(3R, 5S)-dihydroxy-hept-6-enoic acid calcium salt and hydrates thereof, which are prepared by dissolving amorphous Rosuvastatin calcium form in a mixture of water and an organic solvent such as acetone or acetonitrile under heating and then cooling the solution to precipitate crystalline Form A.

WO 2005/023779 discloses another crystalline form, hereafter referred to as Form B of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt which is prepared by slurrying of Amorphous Rosuvastatin calcium in water at 40° C. to get crystalline Form B. US20080194604 describes another new process for the preparation.

US 20080194604 discloses another crystalline form, hereafter referred to as Form C of 7-[4-(4-flurophenyl)-6-isopropyl-2-(N-methyl-N-methylsulfonylamino)-pyrimidin-5-yl]-(3R,5S)-dihydroxy-hept-6-enoic acid calcium salt.

Crystalline forms often show desired different physical and/or biological characteristics which may assist in the manufacturing or formulation of the active compound, to the purity levels and uniformity required for regulatory approval. Crystalline forms of such active compounds may also possess improved pharmacological characteristics, for example, improved bioavailability, and therefore, novel crystalline forms offer enhanced possibilities to modulate and design improved drug products. As crystalline forms A, B, C etc of Rosuvastatin calcium involves very tedious processes which are difficult to use at plant level since the material becomes sticky when stirred initially, results dull colour of material and the product does not crystallize after adding anti-solvent if dissolved in the solvent used. Some of these forms have very high water content which can affect the stability of the product, therefore there was a need for other crystalline forms of 7-[4-(4-flurophenyl)-6-isopropyl-2-(N-methyl-N-methyl sulfonylamino)-pyrimidin-5-yl]-(3R,5S)-dihydroxy-hept-6-enoic acid calcium salt or Rosuvastatin Calcium of improved colour having low water content & simplified process which is easy to handle at plant level, to have a sufficient diversity on crystalline materials to optimize manufacture, formulation and biological efficiency.

SUMMARY OF INVENTION

This invention provides novel highly pure and stable crystalline forms hereinafter referred to as form M and Form M2 of -[4-(4-flurophenyl)-6-isopropyl-2-(N-methyl-N-methylsulfonylamino)-pyrimidin-5-yl]-(3R,5S)-dihydroxy-hept-6-enoic acid Calcium salt or Rosuvastatin calcium and process for its manufacturing. Furthermore the invention also reports the novel processes for the preparation of stable crystalline as well as amorphous Rosuvastatin calcium as confirmed by their XRD as well as stability data.

BRIEF DESCRIPTION OF DRAWINGS

FIG. 1 is a XRD diffractogram of Rosuvastatin calcium form M Ratio 10:5 of Acetone:water.

FIG. 2 is a XRD diffractogram of amorphous Rosuvastatin calcium.

FIG. 3 is a XRD diffractogram of Rosuvastatin calcium form M2.

FIG. 4 is a XRD diffractogram of Rosuvastatin calcium form M Ratio 5:5 of Acetone:water.

DETAILED DESCRIPTION OF THE INVENTION

The main aspect of the present invention is to provide a new crystalline polymorphic forms of 7-[4-(4-flurophenyl)-

6-isopropyl-2-(N-methyl-N-methylsulfonylamino)-pyrimidin-5-yl]-(3R,5S)-dihydroxy-hept-6-enoic acid Calcium salt (Rosuvastatin Calcium) of high purity which exhibits a characteristic X-Ray diffraction pattern with characteristic peaks expressed in $2^\ominus$ values & relative intensity as given below in tabular form), hereinafter designated as form M. XRD diffractogram of Rosuvastatin calcium form M is attached as FIG. 1.

| 2- Theta | Relative intensity (%) (only greater then 40% mentioned) |
|---|---|
| 6.83 | 63 |
| 8.14 | 49 |
| 9.15 | 73 |
| 10.23 | 43 |
| 11.30 | 95 |
| 15.60 | 42 |
| 17.82 | 48 |
| 19.17 | 100 |
| 19.44 | 68 |
| 20.30 | 80 |
| 20.82 | 80 |
| 22.01 | 65 |
| 22.85 | 74 |
| 24.14 | 56 |
| 24.56 | 40 |

According to another aspect of the present invention, a process for highly pure novel crystalline form M of Rosuvastatin Calcium of formula I which comprises:
a) Hydrolysis of Rosuvastatin tert butyl or methyl ester of formula II in presence of aq. Caustic solution in methanol.

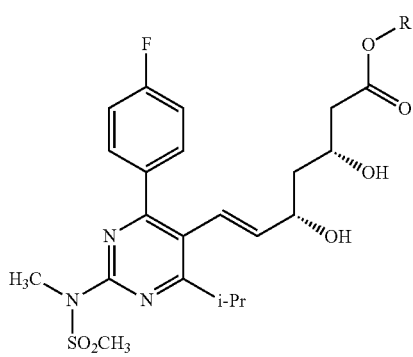

R = Methyl or tert-butyl

Chemical Name: tert-Buty or methyl-(6E)-7-[4-(4-fluorophenyl)-6-isopropyl-2-[methyl(methylsulfonyl) amino] pyrimidin-5-yl]-(3R,5S)-3,5-dihydroxyhept-6-enoate Formula II b) Washing of reaction mass with methyl tert butyl ether.
c) treatment of aq. layer with hydrochloric acid followed by addition of calcium chloride to the reaction mass.
d) isolation of Rosuvastatin calcium by filtration & optionally drying.
e) dissolution of Rosuvastatin calcium (dry or wet) material in an aliphatic ketone.
f) crystallization of material by adding water.
g) filtration of resulting solid followed by drying to get new polymorphic form of Crystalline Rosuvastatin calcium designated as form M.

According to another aspect, the ketone used is selected from acetone, ethyl methyl ketone, diethyl ketone, dipropyl ketone, dibutyl ketone or a mixture thereof & water.

According to one more aspect of current invention, The ratio of aliphatic Ketone used in step e) & Water used in step f) can be 10:5, 5:5 or even 3:8.

According to another aspect of the present invention, a process for highly pure novel crystalline form M of Rosuvastatin Calcium of formula I which comprises:
a) Deprotection of Rosuvastatin diprotected tert butyl ester of formula III in acetonitrile using dil Hydrochloric acid at room temperature.

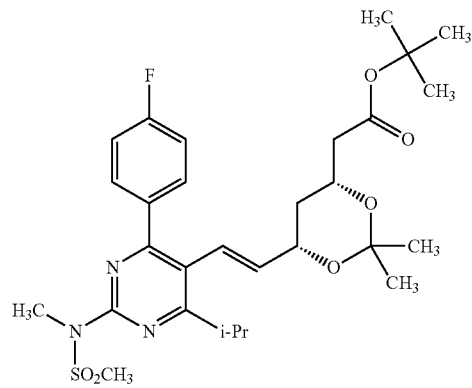 [SMILES: CC(C)c1nc(N(C)S(C)(=O)=O)nc(-c2ccc(F)cc2)c1/C=C/[C@@H]1C[C@H](CC(=O)OC(C)(C)C)OC(C)(C)O1]

Chemical Name: tert-butyl-2-((4R,6S)-6-((E)-2-(4(-(4-fluorophenyl)-6-isopropyl-2-(N-methyl methyl sulphonamido)pyrimidin-5-yl) vinyl)-2,2-dimethyl-1,3-dioxan-4-yl)acetate Formula III b) Confirmation of reaction completion after 2-4 hours via TLC/HPLC.
c) Hydrolysis of reaction mass in presence of aq. Caustic solution.
d) Again confirmation of reaction completion after 4-5 hours via TLC/HPLC.
e) Complete recovery of solvent using vacuum
f) Addition of water & methyl tert butyl ether and stirring for 10-15 min.
g) Layer separation
h) Slow addition of calcium chloride solution to reaction mass
i) Stirring for 4-6 hours
j) Isolation of product via filtration & drying at 50-60° C.
k) Dissolution of Rosuvastatin calcium (dry or wet) of step j) in an aliphatic ketone.
l) Crystallization of material by adding water.
m) filtration of resulting solid followed by drying to get new polymorphic form of Crystalline Rosuvastatin calcium designated as form M.

According to another aspect, the ketone used is selected from acetone, ethyl methyl ketone, diethyl ketone, dipropyl ketone, dibutyl ketone or a mixture thereof.

According to one more aspect of current invention, the ratio of aliphatic Ketone used in step e) & Water used in step f) can be 10:5, 5:5 or even 3:8.

According to one more aspect of current invention, the form M is stable at 30° C. with 65% RH for 48 months & 40° C. with 75% RH for 6 months for all ICH/EP/USP grade. The stability data is as shown in the table below.

| Storage condition | Storage Period (Months) | Description | Assay (OAB) | Related Substances (HPLC) | | | | | | | | | Water |
|---|---|---|---|---|---|---|---|---|---|---|---|---|---|
| | | | | Anti-Isomer | Lactone | Methyl Ester | Tert Butyl Ester | Diprotected | RT-08 | RT-07 | Individual Unknown Imp. | Total Imp. | |
| | | | | | | | Limits → | | | | | | |
| | | A White to creamish solid | 98.0-102.0% w/w | NMT 0.15% | NMT 0.15% | NMT 0.15% | NMT 0.15% | NMT 0.15% | NMT 0.15% | NMT 0.15% | NMT 0.1% | NMT 1.5% | NMT 8.0% |
| | Initial | A white solid | 100.08 | ND | 0.02 | ND | ND | ND | ND | 0.05 | 0.02 | 0.13 | 5.06 |
| 40° C./75% RH | 1 | A white solid | 100.03 | ND | 0.04 | ND | ND | ND | ND | 0.05 | 0.03 | 0.14 | 5.65 |
| | 2 | A white solid | 99.93 | ND | 0.04 | ND | ND | ND | ND | 0.05 | 0.02 | 0.15 | 5.59 |
| | 3 | A white solid | 100.03 | ND | 0.04 | ND | ND | ND | ND | 0.05 | 0.02 | 0.13 | 5.66 |
| | 6 | A white solid | 99.59 | ND | 0.04 | ND | ND | ND | ND | 0.04 | 0.02 | 0.12 | 5.63 |
| 30° C./65% RH | 3 | A white solid | 99.58 | ND | 0.05 | ND | ND | ND | ND | 0.05 | 0.02 | 0.16 | 5.30 |
| | 6 | A white solid | 99.54 | ND | 0.04 | ND | ND | ND | ND | 0.05 | 0.04 | 0.14 | 5.43 |
| | 9 | A white solid | 99.33 | ND | 0.04 | ND | ND | ND | ND | 0.05 | 0.02 | 0.14 | 5.44 |
| | 12 | A white solid | 99.55 | 0.04 | 0.05 | ND | ND | ND | ND | 0.06 | 0.02 | 0.17 | 5.55 |
| | 18 | A white solid | 99.70 | 0.03 | 0.04 | ND | ND | ND | ND | 0.05 | 0.02 | 0.16 | 5.57 |
| | 24 | A white solid | 99.81 | 0.04 | 0.04 | ND | ND | ND | ND | 0.05 | 0.02 | 0.15 | 5.72 |
| | 36 | A white solid | 99.75 | 0.04 | 0.04 | ND | ND | ND | ND | 0.05 | 0.02 | 0.16 | 5.74 |
| | 48 | A white solid | 99.66 | 0.05 | 0.04 | ND | ND | ND | ND | 0.05 | 0.02 | 0.16 | 5.90 |

According to yet another important aspect of current invention, the anti-isomer content in Rosuvastatin calcium is very low or even not detected in comparison to other processes reported in prior art.

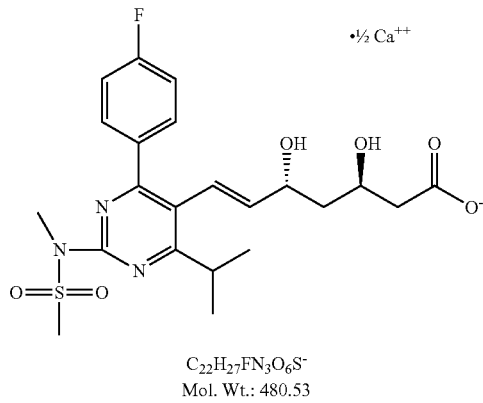

(Formula IV)

$C_{22}H_{27}FN_3O_6S^-$
Mol. Wt.: 480.53
Rosuvastatin Calcium Anti-Isomer (Intermediate A)

4-(4-fluorophenyl)-6-isopropyl-2-[(N-methyl-N-methylsulfonyl)amino]pyrimidine-5-yl-methanol
Mol For: $C_{16}H_{20}O_3FN_3S$
For Wt: 353.41

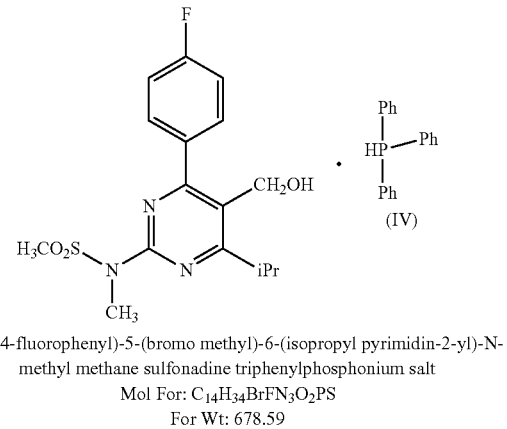

(Intermediate B)

(IV)

N-[4-(4-fluorophenyl)-5-(bromo methyl)-6-(isopropyl pyrimidin-2-yl)-N-methyl methane sulfonadine triphenylphosphonium salt
Mol For: $C_{14}H_{34}BrFN_3O_2PS$
For Wt: 678.59

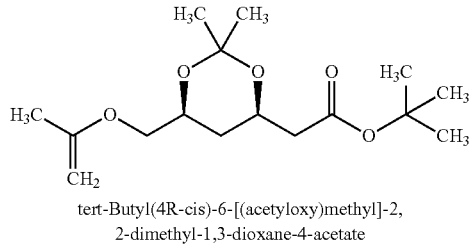

(Intermediate C)

tert-Butyl(4R-cis)-6-[(acetyloxy)methyl]-2,2-dimethyl-1,3-dioxane-4-acetate
CAS# 154026-95-6
Mol For: $C_{15}H_{26}O_6$
For Wt: 302.36

-continued

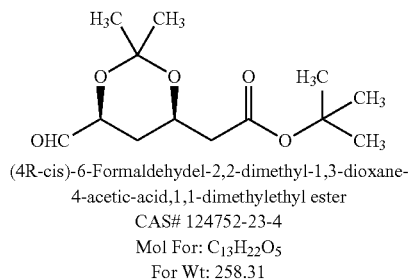

(Intermediate D)

(4R-cis)-6-Formaldehydel-2,2-dimethyl-1,3-dioxane-
4-acetic-acid,1,1-dimethylethyl ester
CAS# 124752-23-4
Mol For: $C_{13}H_{22}O_5$
For Wt: 258.31

According to still another aspect of the present invention, a novel process for preparation of stable amorphous Rosuvastatin Calcium which comprises:
a) dissolution of any crystalline form of Rosuvastatin calcium in a halogenated hydrocarbon such as methylene dichloride, chloroform, carbon tetrachloride or mixture thereof.
b) partial recovery of halogenated hydrocarbon & addition of anti-oxidant like butylated hydroxyanisole, butylated hydroxytoluene or propyl gallate etc.
c) lowering of temperature of organic layer to 10-20° C.
d) addition of an aliphatic ether as anti solvent for crystallization of material.
e) further stirring for complete crystallization of material at 10-20° C.
f) isolation of material by filtration followed by drying at 50-60° C. for 30-40 hours to get amorphous Rosuvastatin calcium as confirmed by XRD pattern in FIG. 2.

According to yet another aspect of present invention the aliphatic ether used is selected from Diisopropylether, methyl tert butyl ether, dimethyl ether, diethyl ether or mixture thereof.

According to still another aspect of the present invention, a novel process for preparation of stable amorphous Rosuvastatin Calcium which comprises:
a) dissolution of any crystalline form of Rosuvastatin calcium in a aliphatic ketone.
b) partial recovery of the aliphatic ketone & addition of anti-oxidant like butylated hydroxyanisole, butylated hydroxytoluene or propyl gallate etc.
c) lowering of temperature of organic layer to 10-20° C.
d) addition of an aliphatic ether as antisolvent for crystallization of material.
e) further stirring for complete crystallization of material at 10-20° C.
f) isolation of material by filtration followed by drying at 50-60° C. for 30-40 hours to get amorphous Rosuvastatin calcium as confirmed by XRD pattern in FIG. 2.

According to another aspect the aliphatic ketone used is selected from acetone, ethyl methyl ketone, diethyl ketone, dimethyl ketone, dipropyl ketone, dibutyl ketone or mixture thereof and aliphatic ether used is selected from Diisopropylether, methyl tert butyl ether, dimethyl ether, diethyl ether or mixture thereof.

According to still another aspect of the present invention, a novel process for preparation of amorphous Rosuvastatin Calcium which comprises:
a) stirring of crystalline form M of Rosuvastatin calcium in a water.
b) Addition of sodium hydroxide solution & heating the reaction mass to 35-40° C.
c) Stirring for 30-60 minutes.
d) Washing with aliphatic ether followed by layer separation.
e) pH of aqueous layer containing product is adjusted to 8.5-9.5 at 25-30° C.
f) addition of calcium chloride solution in water.
g) Stirring to ensure complete crystallization,
h) Drying at 50-60° C. for 10-15 hours.
i) Slurry washing of dried material in aliphatic ether containing anti-oxidant/stabilizer like butylated hydroxyanisole or butylated hydroxytoluene etc.
j) Re-filtered material & dried wet cake at 50-60° C. to get stable amorphous Rosuvastatin calcium as confirmed by XRD pattern in FIG. 2.

According to another aspect the aliphatic ether used in step d) & i) is selected from Diisopropylether, methyl tert butyl ether, dimethyl ether, diethyl ether or mixture thereof.

One more embodiment of the present invention is to provide a new crystalline polymorphic form of 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt (Rosuvastatin Calcium) of high purity which exhibits a characteristic X-Ray diffraction pattern with characteristic peaks expressed in $2^\theta$ values & relative intensity as given below in tabular form), hereinafter designated as form M2.

XRD diffractogram of Rosuvastatin calcium form M2 is attached as FIG. 3 of two different sample.

| 2-θ | Relative intensity (%) (only greater then 40% mentioned) |
|---|---|
| 31.6 | 100 |
| 45.4 | 44 |

According to yet another embodiment, A novel process for the preparation of stable Rosuvastatin Calcium crystalline Form M2 for the compound 7-[4-(4-flurophenyl)-6-isopropyl-2-(N-methyl-N-methyl sulfonyl amino)pyrimidin-5-yl]-(3R,5S)-dihydroxy-hept-6-enoic acid Calcium salt is disclosed, which comprises:
a) Stirring of new polymorphic form 'M' as disclosed in previous embodiment, in water.
b) Heating the reaction mass to 35-40° C., followed by addition of aq. caustic solution
c) Stirring of reaction mass for one hour
d) Addition of aliphatic ether selected from Diisopropyl ether, methyl tert butyl ether, dimethyl ether, diethyl ether or mixture thereof,
e) Layer separation
f) Adjusted pH of aq. layer to 8.5-9.5 with dilute Hydrochloric acid
g) Addition of calcium chloride solution followed by stirring to ensure complete crystallization.
h) Isolation of product as wet cake
i) Drying of wet cake for 10-15 hours at temperature <60° C.
j) Slurry washing of dried material of step i) with aliphatic ether selected from Diisopropyl ether, methyl tert butyl ether, dimethyl ether, diethyl ether or mixture thereof, containing anti-oxidant/stabilizer like butylated hydroxyanisole, butylated hydroxytoluene or propyl gallate etc.
k) Filtration & drying of material at 50-60° C. to get stable Crystalline Form M2 of Rosuvastatin calcium.

According to still another embodiment of current invention, The form M2 is stable at 30° C. with 65% RH for 24 months & 40° C. with 75% RH for 6 months for all ICH/EP/USP grade. The stability data is as shown in the table below.

| | Plant Batch 01 | | | | | | | Plant Batch 02 | | | | | | |
|---|---|---|---|---|---|---|---|---|---|---|---|---|---|---|
| | HPLC Purity (%) | Anti-isomer (%) | Lactone (%) | Keto Imp. (%) | Other impurities (at RRT) | Assay (%) | MC (%) | HPLC Purity (%) | Anti-isomer (%) | Lactone (%) | Keto Imp (%) | Other impurities (at RRT) | Assay (%) | MC (%) |
| Initial Results | 99.85 | 0.04 | 0.03 | ND | 0.02%(0.86), 0.06%(1.48) | 100.19 | 4.10 | 99.82 | 0.05 | 0.03 | ND | 0.02%(0.86), 0.06%(1.48), 0.02%(1.86) | 100.69 | 4.75 |
| Analytical results of RT (after 3 M) | 99.72 | 0.05 | 0.04 | 0.14 | 0.03%(0.29), 0.02%(0.86) | — | — | 99.72 | 0.05 | 0.03 | 0.09 | 0.02% (0.13), 0.02% (0.86), 0.04%(1.53), 0.02% (2.01) | — | — |
| Analytical results of RT (after 6 M) | 99.29 | 0.04 | 0.03 | 0.55 | 0.02%(0.43), 0.02%(0.86), 0.03%(1.52), 0.02%(1.74) | — | — | 99.59 | 0.05 | 0.04 | 0.22 | 0.02% (0.43), 0.02% (0.86), 0.04% (1.52), 0.02% (1.97) | — | — |
| Analytical results of RT (after 9 M) | 99.08 | 0.05 | 0.03 | 0.74 | 0.03%(0.43), 0.02%(0.86), 0.03%(1.53), 0.02%(1.78) | 99.51 | 4.25 | 99.43 | 0.05 | 0.04 | 0.38 | 0.03%(0.43), 0.02%(0.86), 0.03%(1.53), 0.02%(2.01) | 99.66 | 4.85 |
| Analytical results of RT (after 12 M) | 99.00 | 0.06 | 0.03 | 0.79 | 0.04%(0.43), 0.02%(0.86), 0.03%(1.53), 0.02%(1.77), 0.02%(1.80) | 99.65 | 4.35 | 99.39 | 0.07 | 0.04 | 0.40 | 0.03%(0.43), 0.02%(0.86), 0.03%(1.54), 0.02%(2.04) | 99.77 | 4.85 |

According to one more embodiment of current invention, A novel process for the preparation of Amorphous Rosuvastatin calcium using Form M2 is disclosed, which comprises a) Charging of crystalline form M2 of 7-[4-(4-flurophenyl)-6-isopropyl-2-(N-methyl-N-methyl sulfonylamino)-pyrimidin-5-yl]-(3R,5S)-dihydroxy-hept-6-enoic acid Calcium salt or Rosuvastatin calcium in 5-10 times water.

b) Stirring at 30-35° C. for 30-60 minutes.

c) Isolation of amorphous Rosuvastatin calcium by routine filtration & drying at 50-60° C.

The above mentioned invention is supported by the following non limiting examples.

EXAMPLES

Example 1

Preparation of 7-[4-(4-flurophenyl)-6-isopropyl-2-(N-methyl-N-methylsulfonylamino)-pyrimidin-5-yl]-(3R,5S)-dihydroxy-hept-6-enoic Acid Calcium Salt 100 g of tert-Butyl-(6E)-7-[4-(4-fluorophenyl)-6-isopropyl-2-[methyl(methylsulfonyl) amino]pyrimidin-5-yl]-(3R,5S)-3,5-dihydroxyhept-6-enoate) was dissolved 1.0 liter of methanol. The resulting solution was stirred for 10-30 min followed by addition of 10% of caustic solution. The reaction mass is stirred for 3-4 hours followed by reaction monitoring by HPLC/TLC. The solvent was recovered under vacuum to give crude product. Water 1.0 L added to the resulting crude and stirred reaction mass. Methyl tertiary butyl ether 400 ml is added & reaction mass is stirred for 15-20 minutes. The layer is separated and aqueous layer is filtered through celite bed followed by addition of 20% calcium chloride solution (100 ml). The resulting suspension is stirred for 3-4 hours filtered & washed with water. The material is dried at 50-60° C. to afford 90.0 g of Rosuvastatin Calcium.

Example 2

Preparation of 7-[4-(4-flurophenyl)-6-isopropyl-2-(N-methyl-N-methylsulfonylamino)-pyrimidin-5-yl]-(3R,5S)-dihydroxy-hept-6-enoic Acid Calcium Salt Polymorphic Form M To 90 g of 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt prepared in example 1 is dissolved in 900 ml acetone followed by its filtration via hyflow bed. The resulting mass is taken a clean and dried round bottom flask. Water 500 ml is added to the filtered mass. The resulting mass is stirred for 6-10 hours. The resulting suspension is filtered and dried at 50-60° C. to afford 63.0 g of 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt Polymorphic form M. (Water content=3.18% & HPLC Purity=99.79%).

Example 3

Preparation of 7-[4-(4-flurophenyl)-6-isopropyl-2-(N-methyl-N-methylsulfonylamino)-pyrimidin-5-yl]-(3R,5S)-dihydroxy-hept-6-enoic Acid Calcium Salt Polymorphic Form M To 90 g of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt prepared in example 1 is dissolved in 450 ml acetone followed by its filtration via hyflow bed. The resulting mass is taken a clean and dried round bottom flask. Water 450 ml is added to the filtered mass. The resulting mass is stirred for 6-10 hours. The resulting suspension is filtered and dried at 50-60° C. to afford 63.0 g of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt Polymorphic form M. (Water content=3.26% & HPLC Purity=99.85%).

Example 4

Preparation of 7-[4-(4-flurophenyl)-6-isopropyl-2-(N-methyl-N-methylsulfonylamino)-pyrimidin-5-yl]-(3R,5S)-dihydroxy-hept-6-enoic Acid Calcium Salt Polymorphic Form M To 90 g of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt prepared in example 1 is dissolved in 270 ml acetone followed by its filtration via hyflow bed. The resulting mass is taken a clean and dried round bottom flask. Water 630 ml is added to the filtered mass. The resulting mass is stirred for 6-10 hours. The resulting suspension is filtered and dried at 50-60° C. to afford 63.0 g of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt Polymorphic form M. (Water content=3.26% & HPLC Purity=99.85%).

Example 5

Example no 1 & hence 2, 3 & 4 are repeated using 7-[4-(4-fluorophenyl)-6-isopropyl-2-(N-methyl-N-methyl sulfonyl amino) pyrimidine-5-yl]-(3R,5S)-dihydroxy-5-oxo (E)-6-heptenate as starting raw material to get new polymorphic form M of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt or Rosuvastatin calcium. (Water content=4.42% & HPLC purity=99.76%).

Example 6

100 gm of 4-(4-fluorophenyl)-6-isopropyl-2-[(N-methyl-N-methylsulfonyl)amino]pyrimidine-5-yl-methanol (Intermediate A) is dissolved in mixture of Toluene (800 ml) & Acetonitrile (400 ml) at 10-30° C. Then reaction mass is cooled to 15-20° C. followed by addition of Potassium tribromide (14 ml). The reaction mass is then stirred at 15-20° C. for 30 minutes. The completion of reaction is confirmed via TLC/HPLC. After completion of reaction, reaction mass is quenched in water & the crude product is recovered by recovery of solvent under vacuum. This crude material is taken in toluene (100 ml) followed by stirring to get clear solution. Then this reaction mass is heated to 80-90° C. followed by slow addition of Triphenylphosphine (72 g) in toluene. The reaction mass is refluxed for 10-12 hours at 105-110° C. till reaction completion. After reaction completion the reaction mass is cooled to RT followed by stirring for 1 hour & filtration, so as to obtained product as wet cake. This wet cake is dried at 65-70° C. under vacuum to get N-[4-(4-fluorophenyl)-5-(bromomethyl)-6-(isopropyl pyrimidin-2-yl)-N-methyl methane sulfonamide triphenylphosphoniumsalt (Intermediate B) having HPLC purity=99.85%.

Example 7

100 gm of tert-Butyl(4R-cis)-6-[(acetyloxy)methyl]-2,2-dimethyl-1,3-dioxane-4-acetate (Intermediate C) is dissolved in methanol (400 ml) & cooled the reaction mass to 0-5° C. under stirring. Then potassium carbonate is added to reaction mass followed by stirring at 0-5° C. The reaction mass is then stirred at 0-5° C. for three hours till reaction completion. Complete recovery of solvent is done under vacuum to get crude product, which is then taken in methylene chloride (350 ml) and water washed organic layer followed by layer separation. The organic layer is recovered under vacuum to get (4R-cis)-6-hydroxymethyl-2,2-dimethyl-1,3-dioxane-4-acetic-acid,1,1-dimethylethyl ester (RTS05). This intermediate is then taken again in methylene chloride (500 ml) followed by charging of 2,2,6,6,-tetramethylpiperidinooxy (1 g) & Potassium bromide (10 g). To this reaction mass we add up mixture of 10% sodium bicarbonate (16.25 g) solution & Sodium hypochlorite (280 ml; 10-12%) at −10 to −15° C. The reaction is continued at this temperature for 2 hours so as to complete reaction. After reaction completion reaction mass is quenched in sodium Thiosulphate (25 g) solution in water, followed by stirring & layer separation. The aqueous layer containing product is then extracted with methylene chloride (100 ml). After that methylene chloride layer is recovered under vacuum to give 68 g (4R-cis)-6-Formaldehydel-2,2-dimethyl-1,3-dioxane-4-acetic-acid,1,1-dimethylethyl ester (Intermediate D) as desired product having HPLC purity=86.33%.

Example 8

100 gm of N-[4-(4-fluorophenyl)-5-(bromomethyl)-6-(isopropyl pyrimidin-2-yl)-N-methyl methanesulfonamide-triphenylphosphoniumsalt (Intermediate B) is taken in dimethylsulphoxide (400 ml) under stirring and potassium carbonate (76 g) is added to it followed by addition of 50 g (4R-cis)-6-Formaldehydel-2,2-dimethyl-1,3-dioxane-4-acetic-acid, 1,1-dimethylethyl ester (Intermediate D) at room temperature. The reaction mass is then heated to 70-80° & stirred for 7-8 hours. After reaction completion temperature is reduced to 50° C. followed by addition of toluene. The reaction mass is now stirred for 1 hour at 25-35° C., followed by layer separation. The organic layer is washed twice with water (700 ml). Then organic layer is recovered so as to be left with ¼ of the original volume. Then addition of hexanes (600 ml) is done for crystallization of product at 50-60° C. The reaction mass is stirred at this temperature followed by cooling to reaction mass to 0-5° C. for filtration. The wet cake is dried at 40-50° C. for 4-6 hours to give 80 g tert-butyl-2-((4R,6S)-6-((E)-2-(4(-(4-fluorophenyl)-6-isopropyl-2-(N-methylmethylsulphonamido)pyrimidin-5-yl) vinyl)-2,2-dimethyl-1,3-dioxan-4-yl)acetate (Compound of Formula III) having HPLC purity=97.98%.

Example 9

100 gm of tert-butyl-2-((4R,6S)-6-((E)-2-(4(-(4-fluorophenyl)-6-isopropyl-2-(N-methyl methyl sulphonamido)pyrimidin-5-yl) vinyl)-2,2-dimethyl-1,3-dioxan-4-yl)acetate (Compound of Formula III) is dissolved in Acetonitrile (500 ml) followed by stirring for 10-30 min. This is followed by addition of dilute hydrochloric acid. Then reaction mass is stirred for 2-4 hours till reaction completion. After confirmation of reaction completion by TLC/HPLC, caustic solution is added to reaction mass and further stirred reaction mass to 3-4 hours. Then after completion of second reaction, solvent is completely removed under vacuum at slightly elevated temperature. This is followed by addition of first water (1000 ml) & then methyl tertiary butyl ether (400 ml) & stirred so as to provide washing to product. Then layer separation is done and aq. layer containing product is filtered via celite bed. This is followed by dropwise addition of Calcium chloride solution & stirring for 4-6 hours to ensure complete crystallization. Then material is filtered & dissolved in Acetone (500 ml). Then water (500 ml) is added to reaction mass and stirred reaction mass for 6-10 hours. The resulting suspension is filtered and dried at 50-60° C. to afford 59.0 g of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt Polymorphic form M. (Water content=3.22% & HPLC Purity=99.87%, Anti-isomer content (Compound of formula IV)-Nil).

Example 10

100 gm of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt Polymorphic form M is dissolved in 2.0 Liter of Acetone at 10-30° C. or at slight heating to ensure complete dissolution. The solvent is recovered at atmospheric pressure to be left with 500 ml followed by filtration through celite bed. The filtered layer is taken in clean and dry round bottom flask, followed by addition of Butylated hydroxyanisole (0.5 g) and material is crystallized by the addition of methyl tertiary butyl ether. The material is filtered and dried under vacuum at 50-60° C. to afford 84.0 grams of amorphous Rosuvastatin calcium as a white to off-white solid. (Water content=3.05% & HPLC Purity=99.89%)

Example 11

100 gm of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt Polymorphic form M is dissolved in 2.0 Liter of methylene chloride at 10-30° C. or at slight heating to ensure complete dissolution. The solvent is recovered at atmospheric pressure to be left with 500 ml followed by filtration through celite bed. The filtered layer is taken in clean and dry round bottom flask, followed by addition of Butylated hydroxyanisole (0.5 g) and material is crystallized by the addition of diisopropyl ether. The material is filtered and dried under vacuum at 50-60° C. to afford 85.1 grams of amorphous Rosuvastatin calcium as a white to off-white solid. (Water content=3.12% % & HPLC Purity=99.86%)

Example 12

100 gm of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt Polymorphic form M is taken in Water (600 ml), under stirring followed by the addition of sodium hydroxide solution. The reaction mass is stirred at 35-40° C. for 30-60 min followed by slow addition of methyltertbutyl ether (400 ml). Now the reaction is further maintained at this temperature for 30-40 minutes. After stirring reaction mass is settled followed by layer separation. The Aq. layer containing product is filtered via hyflow bed & any traces of solvents present is removed under vacuum. Now the aqueous layer is cooled to 25-30° C. followed by the pH adjustment to 8.5-9.58. Now calcium chloride solution is added dropwise under stirring to ensure proper crystallization. The resulting material is filtered as wet cake followed by its water washing (500 ml). Now the material is dried at 50-60° C. for 10-15 hours. Now this dried material is slurry washed in methyltertbutyl ether (200 ml) containing butylated hydroxy anisole (0.5 g) for 5-10 minutes. The desired product is now isolated as wet cake by filtration. The wet cake is now dried at 50-60° C. to get desired 82.5 g amorphous Rosuvastatin Calcium as an offwhite solid. (Water content=2.91% & HPLC Purity=99.92%).

Example 13

Preparation of Crystalline Form M2 of 7-[4-(4-flurophenyl)-6-isopropyl-2-(N-methyl-N-methyl sulfonylamino)-pyrimidin-5-yl]-(3R,5S)-dihydroxy-hept-6-enoic Acid Calcium Salt Crystalline Form M of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt (100 g) is added to water (600 ml) followed by stirring. To this caustic solution (15 g in 100 ml water) is slowly charged. The resulting mass is then stirred for 60-90 minutes at 25-35° C. After this reaction mass is give washing with methyl tert-butyl ether (300 ml) followed by its layer separation. The aq. layer is kept aside while organic layer is extracted with water (100 ml), again followed by layer separation. Now both the aq. layers are combined and organic layer is discarded. Now aq. layer is heated & traces of methyl tertbutyl ether is now removed under vacuum followed by cooling of aq. layer to room temperature. Now adjust the pH of aq. layer with dil. Hydrochloric acid (0.15 ml HCl in 100 ml of water) to 8.5-9.5. Now calcium chloride solution (20 g in 100 ml water) is slowly added followed by stirring for 30-90 minutes at 25-30° C. Material is isolated as wet cake followed by its drying at temperature 50-60° C. for 10-15 hours. This is followed by slurry washing of dried material in methyl tertiary butyl ether (200 ml) containing butylated hydroxyanisole (0.5 g) for 10-20 minutes. Then final material is filtered & dried at 50-60° C. for 6-10 hours to give Rosuvastatin calcium Crystalline form M2. (Water content=3.95% & HPLC Purity=99.72%). XRD attached FIG. III.

Example 14

Preparation of Amorphous 7-[4-(4-flurophenyl)-6-isopropyl-2-(N-methyl-N-methyl sulfonyl amino)-pyrimidin-5-yl]-(3R,5S)-dihydroxy-hept-6-enoic Acid Calcium Salt Using Crystalline Form M2

Crystalline Form M of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt (100 g) is added to water (1000 ml) water & stirred at 30-35° C. for 30-60 minutes. The material is then isolated by filtration followed by its drying at 50-60° C. to give amorphous 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt. (Water content=3.12% & HPLC Purity=99.83%).

The invention claimed is:
1. A polymorphic crystalline form 'M' of the compound 7-[4-(4-flurophenyl)-6-isopropyl-2-(N-methyl-N-methyl-sulfonylamino)-pyrimidin-5-yl]-(3R,5S)-dihydroxy-hept-6-enoic acid Calcium salt, designated as form 'M' of Rosuvastatin calcium of formula I or hydrates thereof

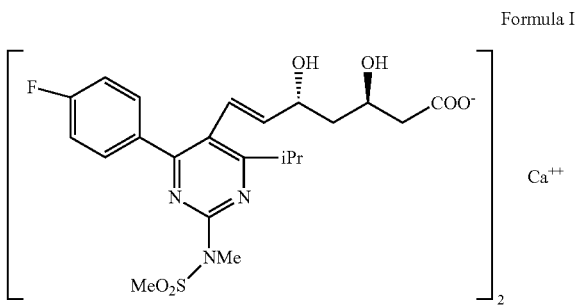

Formula I having characteristic peaks as given below,

| 2- Theta | Relative intensity (%) (Peaks having >70% Intensity are mentioned) |
|---|---|
| 9.15 | 73 |
| 11.30 | 95 |
| 19.17 | 100 |
| 20.30 | 80 |
| 20.82 | 80 |
| 22.85 | 74. |

2. A process for the preparation of highly pure crystalline form 'M' of the compound 7-[4-(4-flurophenyl)-6-isopropyl-2-(N-methyl-N-methyl sulfonyl amino)-pyrimidin-5-yl]-(3R, 5S)-dihydroxy-hept-6-enoic acid Calcium salt or hydrates thereof according to claim 1, which comprises the steps of:
  i. hydrolysis of tert-Butyl or methyl-(6E)-7-[4-(4-fluorophenyl)-6-isopropyl-2-[methyl(methyl sulfonyl)amino]pyrimidin-5-yl]-(3R,5S)-3,5-dihydroxyhept-6-enoate or Rosuvastatin tert butyl/methyl ester in an aliphatic alcohol with an aq. Caustic solution;
  ii. isolation of Rosuvastatin calcium by addition of calcium chloride;
  iii. recrystallization of resulting Rosuvastatin Calcium using an aliphatic ketone selected from acetone, ethyl methyl ketone, diethyl ketone, dipropyl ketone, dibutyl ketone or mixture thereof and water; and
  iv. isolation of Rosuvastatin calcium crystalline form M by filtration and drying.

3. A novel process for the preparation of highly pure crystalline form 'M' of the compound 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt or hydrates thereof according to claim 1, which comprises the steps of:
  i. deprotection of tert-butyl-2-((4R,6S)-6-((E)-2-(4(-(4-fluorophenyl)-6-isopropyl-2-(N-methylmethylsulphonamido)pyrimidin-5-yl)vinyl)-2,2-dimethyl-1,3-dioxan-4-yl)acetate in acetonitrile using dilute hydrochloric acid;
  ii. hydrolysis of resulting material with an aq. Caustic solution;
  iii. complete removal of the acetonitrile from reaction mass under vacuum;
  iv. addition of water and methyl tert-butyl ether;
  v. separation;
  vi. isolation of Rosuvastatin calcium by addition of calcium chloride to aq. layer;
  vii. recrystallization of resulting Rosuvastatin Calcium using an aliphatic ketone selected from acetone, ethyl methyl ketone, diethyl ketone, dipropyl ketone, dibutyl ketone or a mixture thereof and water; and
  viii. isolation of Rosuvastatin calcium crystalline form M by routine filtration and drying.

4. The process of claim 2 wherein in step iii) the ratio of aliphatic Ketone & water can be selected from 10:5, 5:5 or 3:8.

5. The process of claim 3, in which anti-isomer content is very low (<0.1% by HPLC) or even 'Not Detected'.

6. A The process for the preparation of stable amorphous Rosuvastatin Calcium for the compound 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt which comprises:
  i. dissolution of a polymorphic form 'M' of Rosuvastatin calcium in halogenated hydrocarbon such as methylene dichloride, chloroform, carbon tetrachloride or mixture thereof or an aliphatic ketone such as acetone, ethyl methyl ketone, diethyl ketone, dipropyl ketone, dibutyl ketone or a mixture thereof & water;
  ii. recovery of solvent from reaction mass of step (i) to left approximately 5 times the volume w.r.t. the starting material or Rosuvastatin calcium & addition of anti-oxidant/stabilizer like butylated hydroxyanisole, butylated hydroxytoluene or propyl gallate;
  iii. crystallization of amorphous Rosuvastatin Calcium salt by addition of an aliphatic ether which is selected from Diisopropylether, methyl tert butyl ether, dimethyl ether, diethyl ether or mixture thereof; and
  iv. isolation & drying of filtered material to get amorphous Rosuvastatin calcium.

7. A process for the preparation of stable amorphous Rosuvastatin Calcium for the compound 7-[4-(4-flurophenyl)-6-isopropyl-2-(N-methyl-N-methyl sulfonyl amino)-pyrimidin-5-yl]-(3R,5S)-dihydroxy-hept-6-enoic acid Calcium salt which comprises:
  i. stirring of new polymorphic form 'M' of Rosuvastatin calcium in water;
  ii. heating the reaction mass to 35-40° C. by adding aq. caustic solution;
  iii. of reaction mass for 30-40 minutes;
  iv. addition of aliphatic ether aliphatic selected from Diisopropyl ether, methyl tert butyl ether, dimethyl ether, diethyl ether or mixture thereof;
  v. layer separation;
  vi. filtration of aq. layer containing product via hyflow bed;
  vii. adjusted pH of aq. layer to 8.5-9.5 with dilute Hydrochloric acid;
  viii. addition of calcium chloride solution;
  ix. stirring to ensure complete crystallization;
  x. isolation of product as wet cake by filtration;
  xi. slurry washing of wet cake with water;
  xii. drying of wet cake for 10-15 hours at 50-60° C.;
  xiii. slurry washing dried material of step xii) with aliphatic ether selected from Diisopropyl ether, methyl tert butyl ether, dimethyl ether, diethyl ether or mixture thereof, containing anti-oxidant/stabilizer like butylated hydroxyanisole, butylated hydroxytoluene or propyl gallate; and
  xiv. filtration & re-drying of material at 50-60° C. to get stable amorphous Rosuvastatin calcium.

8. A polymorphic crystalline form of the compound 7-[4-(4-fluorphenyl)-6-isopropyl-2-(N-methyl-N-methyl-sulfonylamino)-pyrimidin-5-yl]-(3R,5S)-dihydro xy-hept-6-enoic acid Calcium salt, designated as form 'M2' of Rosuvastatin calcium of formula I or hydrates thereof

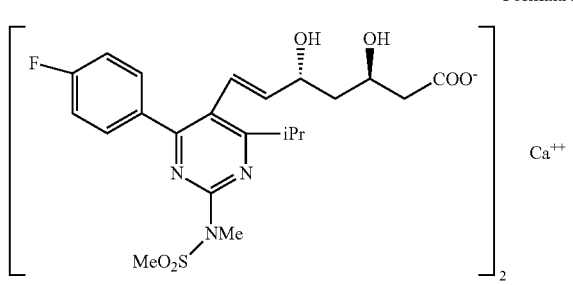

Formula I having characteristic peaks as given below:

| 2- Theta | Relative intensity (%) (Peaks having >40% Intensity are mentioned) |
|---|---|
| 31.6 | 100 |
| 45.4 | 44. |

9. A process for the preparation of stable Rosuvastatin Calcium crystalline Form M2 for the compound 7-[4-(4-flurophenyl)-6-isopropyl-2-(N-methyl-N-methyl sulfonyl amino)pyrimidin-5-yl]-(3R,5S)-dihydroxy-hept-6-enoic acid Calcium salt which comprises:
   a) stirring of new polymorphic form 'M' of Rosuvastatin calcium in water;
   b) heating the reaction mass to 35-40° C. by adding aq caustic solution;
   c) stirring of reaction mass for 30-40 minutes;
   d) addition of aliphatic ether selected from Diisopropyl ether, methyl tert butyl ether, dimethyl ether, diethyl ether or mixture thereof;
   e) layer separation;
   f) filtration of aq. layer containing product via hyflow bed;
   g) adjusted pH of aq. layer to 8.5-9.5 with dilute hydrochloric acid;
   h) addition of calcium chloride solution;
   i) stirring to ensure complete crystallization;
   j) isolation of product as wet cake;
   k) drying of wet cake for 10-15 hours at 50-60° C.;
   l) slurry washing of dried material of step xi) with aliphatic ether selected from Diisopropyl ether, methyl tert butyl ether, dimethyl ether, diethyl ether or mixture thereof, containing anti-oxidant/stabilizer like butylated hydroxyanisole, butylated hydroxytoluene or propyl gallate; and
   m) filtration & drying of material at 50-60° C. to get stable Crystalline Form M2 of Rosuvastatin calcium.

10. The process for the preparation of Amorphous Rosuvastatin calcium using Form M2 of claim 9, which comprises:
   i. charging of crystalline form M2 of 7-[4-(4-flurophenyl)-6-isopropyl-2-(N-methyl-N-methylsulfonylamino)-pyrimidin-5-yl]-(3R,5S)-dihydroxy-hept-6-enoic acid Calcium salt or Rosuvastatin calcium in water (5-10 times);
   ii. stirring at 30-35° C. for 30-60 minutes; and
   iii. isolation of amorphous Rosuvastatin calcium by routine filtration & drying at 50-60° C.

11. The process of claim 10 wherein stabilizers used in the preparation of crystalline form M2 or Amorphous Rosuvastatin calcium to increase their stability are selected from butylated hydroxyanisole, butylated hydroxytoluene, propyl gallate or a mixture thereof.

12. Rosuvastatin calcium polymorphic Form M of claim 1 is stable for 4 years and even more at long term stability condition of 30° C. & 65% RH as well as at accelerated/stress condition of 40-45° C. & 75% RH.

13. Rosuvastatin calcium polymorphic Form M2 of claim 8, is stable for >2 years at long term stability condition of 30° C. & 65% RH as well as at accelerated/stress condition of 40-45° C. & 75% RH.

14. A process of step vii) of claim 3, wherein the ratio of aliphatic Ketone & water can be selected from 10:5, 5:5 or even 3:8.

* * * * *